(12) United States Patent
Williams

(10) Patent No.: US 6,237,194 B1
(45) Date of Patent: May 29, 2001

(54) DEVICES FOR ASSISTING PHYSICALLY HANDICAPPED PERSONS

(76) Inventor: Allen Duane Williams, 2135 W. 89 St., Cleveland, OH (US) 44102

( * ) Notice: Subject to any disclaimer, the term of this patent is extended or adjusted under 35 U.S.C. 154(b) by 0 days.

(21) Appl. No.: 09/450,371

(22) Filed: Nov. 26, 1999

(51) Int. Cl.[7] .......................... A45C 13/22; A45C 13/26; A47J 45/00
(52) U.S. Cl. ..................... 16/430; 16/110.1; 16/422; 16/DIG. 12; 15/443; 30/298; 294/25; 401/6
(58) Field of Search .................. 16/430, 110.1, 16/DIG. 12, 422; 15/443, 143.1, 145; 30/298, 232; 294/25; 81/487, 189, 177.1, 177.3; 401/6, 7, 8, 88; 74/558

(56) References Cited

U.S. PATENT DOCUMENTS

| | | | |
|---|---|---|---|
| 2,709,419 | * 5/1955 | Appel | 401/8 |
| 4,602,885 | 7/1986 | Bischoff et al. | 401/6 |
| 4,846,710 | 7/1989 | Campbell | 434/166 |
| 5,146,810 | * 9/1992 | Mueller | 30/298 |
| 5,310,345 | 5/1994 | Gershon | 434/166 |
| 5,695,231 | * 12/1997 | Hoffman | 294/58 |
| 5,944,433 | * 8/1999 | O'Mara et al. | 401/8 |
| 5,971,642 | * 10/1999 | O'Mara et al. | 401/8 |

* cited by examiner

Primary Examiner—Chuck Y. Mah

(57) ABSTRACT

A device for assisting a physically handicapped person to perform tasks that are managed by the use of a hand of the handicapped person is disclosed. The device has first and second finger rings that allows a device to be easily manipulated during the control of the task being performed by the handicapped person. Also disclosed is a storage container that makes use for the quick-disconnect mechanism of the device allowing for easy accessibility of the device by the physically handicapped person.

8 Claims, 10 Drawing Sheets

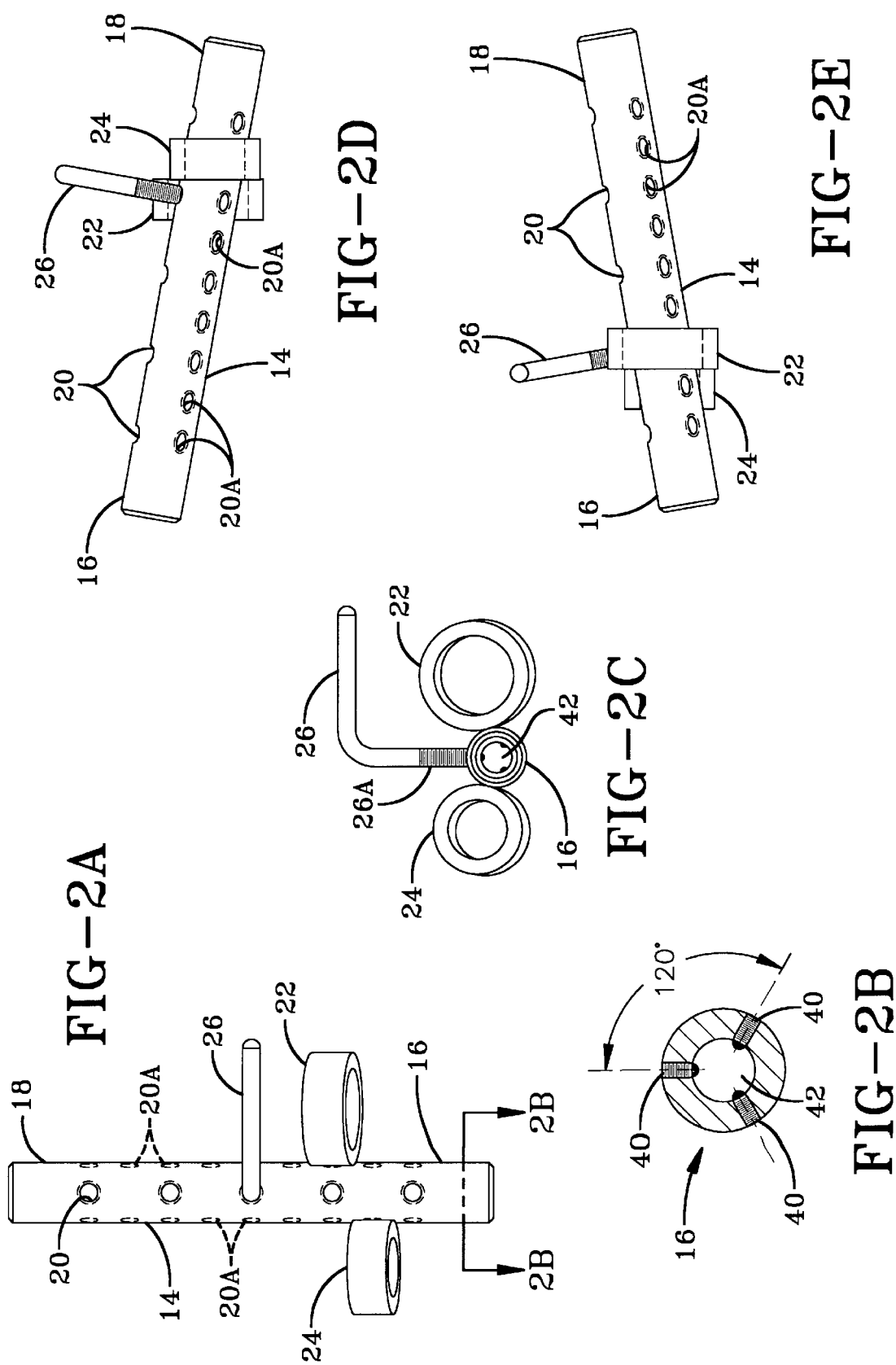

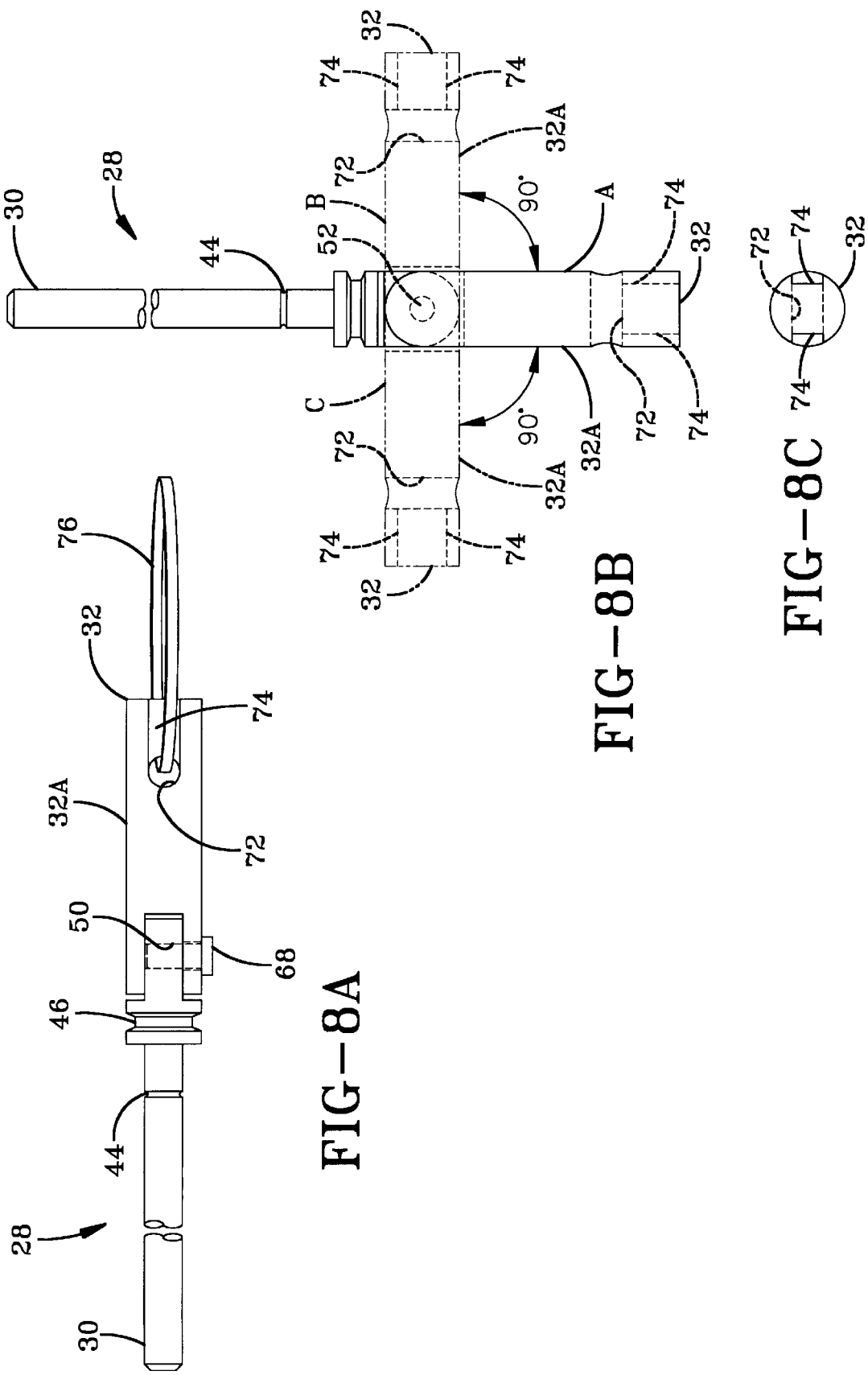

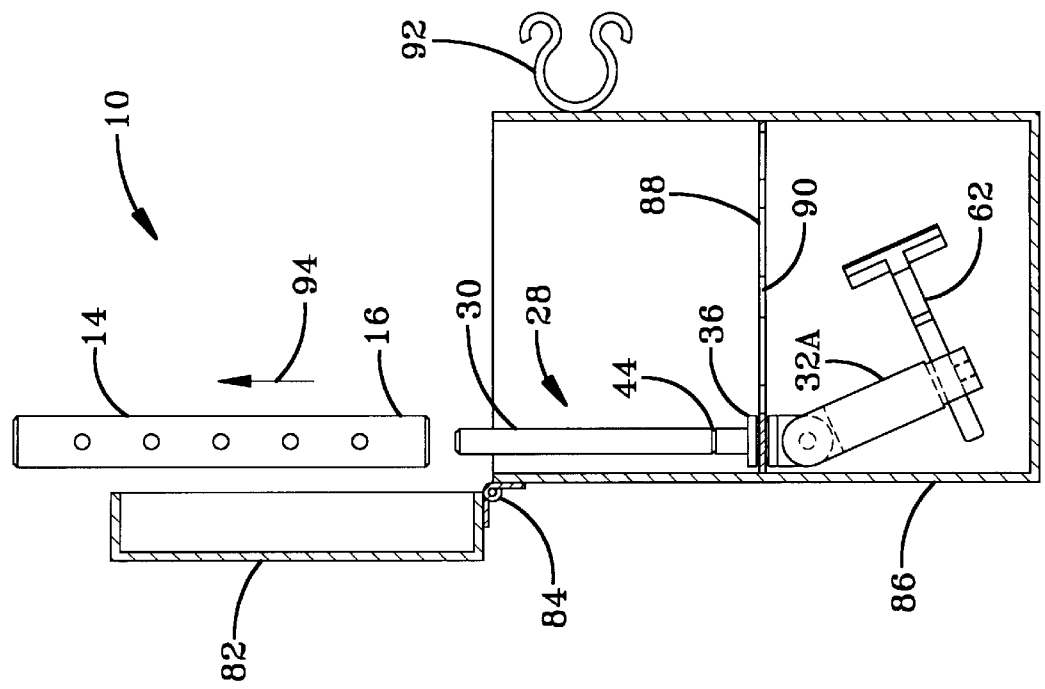
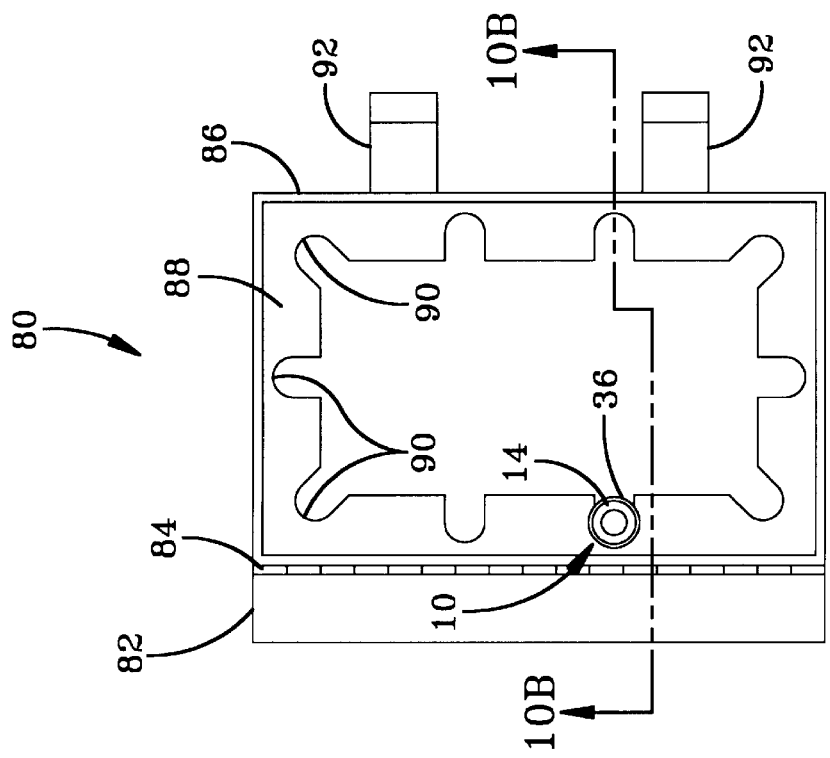

DEVICES FOR ASSISTING PHYSICALLY HANDICAPPED PERSONS

BACKGROUND OF THE INVENTION

1.0 Field of the Invention

The present invention relates to devices for assisting physically handicapped persons to perform tasks that are managed by the use of their hands.

2.0 Description of the Prior Art

Physically handicapped persons, such as paraplegics suffer paralysis of the lower half of the body having involvement with both legs. In addition, physically handicapped people have poor prehensile ability due to brain damage, spinal injury and the like. Frequently, such handicapped people have sufficient control of their arms to carry out any operations, but simply have poor hand controls so that the gripping or grasping required for holding implements to perform tasks is difficult.

The physically handicapped people need encouragement to perform as many activities as his/her physical limitations allow both at home and in the. community. Such encouragement combats the tendency of physically handicapped people to remain isolated. This encouragement may take many forms with one such form being the use of work simplification techniques and uncomplicated aides to assist physically handicapped people to perform different desired tasks, such as those managed by the use of the hands of a handicapped person. It is desired that devices be provided for assisting the physically handicapped persons to perform tasks that are managed by the use of their hands. It is further desired that storage means be provided for these devices which further assist the handicapped person by allowing easy accessibility of the devices by physically handicapped persons.

SUMMARY OF THE INVENTION

Accordingly, it is a primary object of the present invention to provide for devices for assisting a physically handicapped person to perform tasks that are managed by the use of their hands.

It is a further object of the present invention to provide for a chest for storing devices that allow for easy accessibility of the devices by physically handicapped persons.

Another object of the present invention is to provide devices that are easily held and gripped by the handicapped person.

It is still a further object of the present invention to provide for devices having quick-release mechanisms to allow for easy interchanging of holders adaptable for the instruments used to perform tasks by the handicapped persons.

In addition, it is an object of the present invention to provide for a storage box having a shelf that is form fitted for operatively cooperating with the quick-release mechanisms of the devices.

In accordance with these and other objects, the invention provides for a device for assisting a physically handicapped person to perform tasks that are managed by the use of their hands having digits. The device comprises a hollow member, first and second rings, an insert, and a holder. The hollow member has first and second ends and a central bore having predetermined dimensions and extending at least partially therethrough and encompassing the first end thereof. The hollow member has a plurality of apertures having threads therein. The first and second rings are attached to the hollow member and are spaced apart from each other in a predetermined manner and each is dimensioned to receive one of the digits of the hand of a handicapped person. The insert has a threaded end for insertion into and threadedly engaged with anyone of the threaded apertures. The holder has first and second ends with the first end being dimensioned for insertion into the central bore by way of the first end of the hollow member and with the second end thereof having provisions for holding an instrument used in the performance of a task managed by the use of the hand of the handicapped person.

DETAILED DESCRIPTION OF THE DRAWINGS

The foregoing objects and advantages of the present invention will be more fully understood from the following detailed description having reference to the appended drawings wherein:

FIG. 2 is composed of FIGS. 2(A), 2(B), 2(C), 2(D), and 2(E) which cumulatively illustrate the hollow member, first and second rings, and the insert of the device of the present invention;

FIG. 8 is composed of FIGS. 8(A), 8(B), and 8(C) that illustrates details of another embodiment of the holder of the present invention;

FIG. 10 is composed of FIGS. 10(A), and 10(B) that illustrates details of a storage container for holding and advantageously allowing easy access to the devices of the present invention that assist a physically handicapped person.

DETAILED DESCRIPTION OF THE PREFERRED EMBODIMENTS

Figure 1:
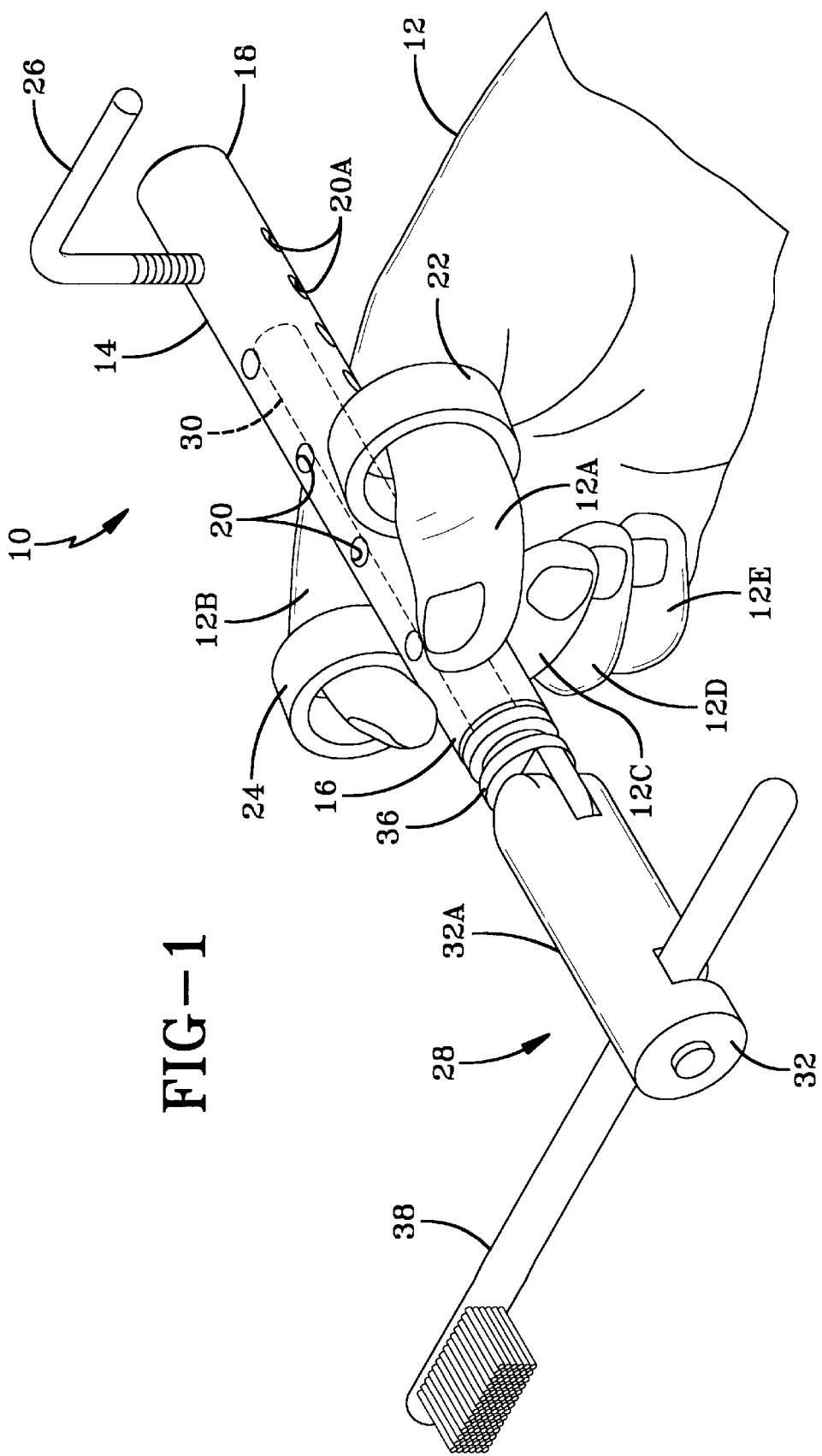
FIG. 1 is a perspective view of the hand of a physically handicapped person holding the device of the present invention.

Referring to the drawings, wherein the same reference number indicates the same element throughout, there is shown in FIG. 1 a perspective view of the device 10 of the present invention being held by a hand 12 of a physically handicapped person so as to perform tasks that are managed by the use of the hand 12 having digits 12A, 12B, 12C, 12D, and 12E.

The device 10 comprises a hollow member 14 having first and second ends 16 and 18, respectively, and a central bore (not shown) having predetermined dimensions and extending at least partially through and encompassing the first end 16. The hollow member 14 has a plurality of apertures 20 each having threads therein, as well as apertures 20A also having threads therein that provide for the means to position finger rings 22 and 24 so as to be fastened along the length of the hollow member 14.

The first and second finger rings 22 and 24, respectively, are preferably threadly engaged to the threads of the apertures 20A, but other appropriate means, such as snap-in devices, to be further described, that may be used to releasably attach the fingers 22 and 24 to the hollow member 14. The first and second rings 22 and 24 are spaced apart from each other in a predetermined manner and each is dimensioned to receive one of the digits of the hand of the handicapped person. More particularly, the first ring 22 is dimensioned to receive the thumb of the hand 12 and the second ring 24 is dimensioned to receive the forefinger of the hand 12 as shown in FIG. 1. The device 10 further comprises an insert 26 having a threaded end for insertion into and for threaded engagement with anyone of the threaded apertures 20. The insert 26 is used for holding and orienting the holder 28 which has a first end 30 (not shown in FIG. 1, but shown in FIG. 3).

The holder 28 has a second end 32 and an intermediate region 34 (not shown in FIG. 1, but shown in FIG. 3) which is located between the first and second ends 30 and 32. The holder 28 has a knuckle arrangement 36, as well as an extension 32A which, in part, serves as means for holding an instrument, such as a toothbrush 38 used in the performance of the task managed by the use of a hand 12 of the handicapped person. The device 10 may be further described with reference to FIG. 2 which is composed of FIGS. 2(A), 2(B), 2(C), 2(D) and 2(E).

FIG. 2(A) further illustrates one of the apertures 20 having the insert 26 threaded engaged therein as well as illustrating two rows of apertures 20A, with one row thereof having the first finger ring 22 inserted therein; and with the other row having the second finger ring 24 inserted therein. As previously mentioned, the first and second finger rings 22 and 24 may be provided with appropriate releasable holding means, such as snap-in devices (not shown), so that each of the first and second finger rings 22 and 24 may be easily rotated with the thumb and forefinger, respectively, inserted therein. The first end 16 of the hollow member 14 comprises at least one spring loaded plunger 40 which may be further described with reference to FIG. 2(B) which is a view taken along the line 2B—2B of FIG. 2(A).

FIG. 2(B) illustrates end 16 as having at least one spring loaded plunger 40, but preferably three spring loaded plungers 40 that are spaced apart from each other by about 120 degrees about the central bore 42 of the hollow member 14. The spring loaded plungers 40 are arranged in the first end 16 so as to frictionally engage a groove 44, to be described, of the holder 28. The holder 28 is also engaged by the insert 26 which may be further described with reference to FIG. 2(C).

FIG. 2(C) in addition to illustrating the insert 26 as having a threaded end 26A, also shows the front view of the hollow member 14 with an orientation of the first and second finger rings 22 and 24. A further orientation of a member 14 is illustrated in FIGS. 2(D) and 2(E) which are side views thereof The member 14 has a central bore 42, previously mentioned, which has predetermined dimensions so as to accept the holder 28 which may be further described with reference to FIG. 3 composed of FIGS. 3(A) and 3(B) that respectively illustrate a side and top view thereof.

Figure 3A:
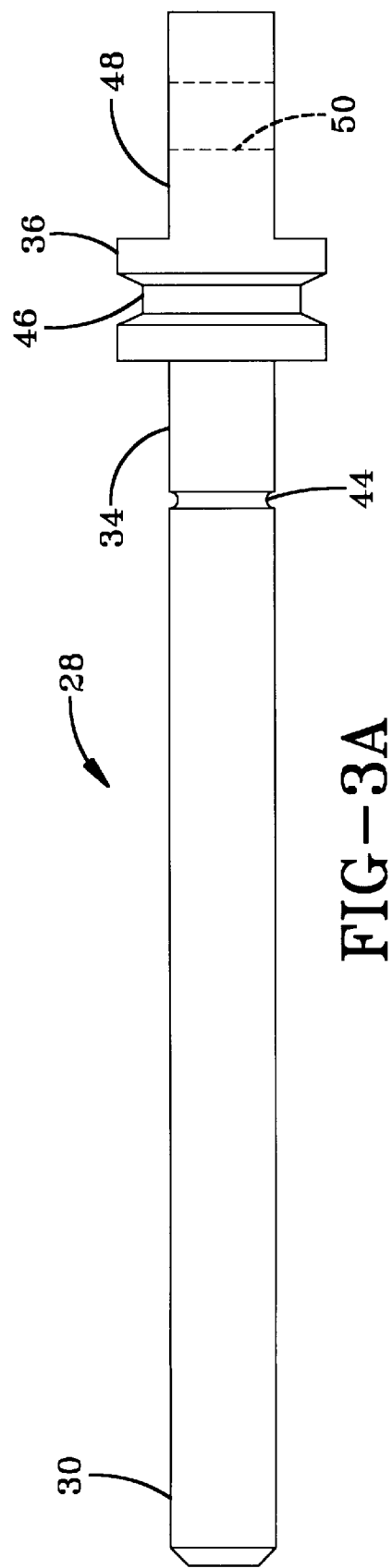
FIG. 3 is composed of FIGS. 3(A), and 3(B) respectively showing a side and top view of the holder of the present invention.
Figure 3B:
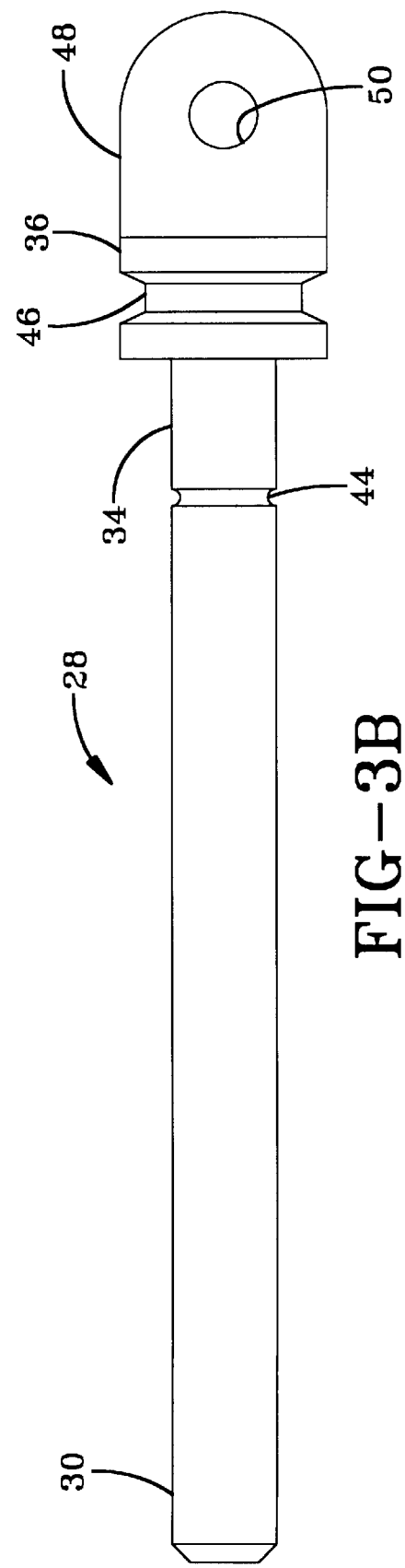

FIGS. 3(A) and 3(B) illustrate the first end 30 and the intermediate region 34 of the holder 28, but does not illustrate the extension 32A shown in FIG. 1, but which will be further described with reference to FIGS. 4, 5, and 6. FIGS. 3(A) and 3(B) illustrate the knuckle arrangement 36 as including a channel 46 and a control region 48 having an opening 50 therein. The groove 44 operatively cooperates with the spring loaded plungers 40, as described with reference to FIG. 2(B), so as to provide for mechanism for the holder 28 to be quickly released from the hollow member 14. The operative cooperation of the hollow member 14 with the holder 28 may be further described with reference to FIGS. 4, 5 and 6 each illustrating the device 10 as being particularly suited for holding and capturing a particular instrument so that the instrument may be more easily manipulated by the physically handicapped person.

Figure 4:
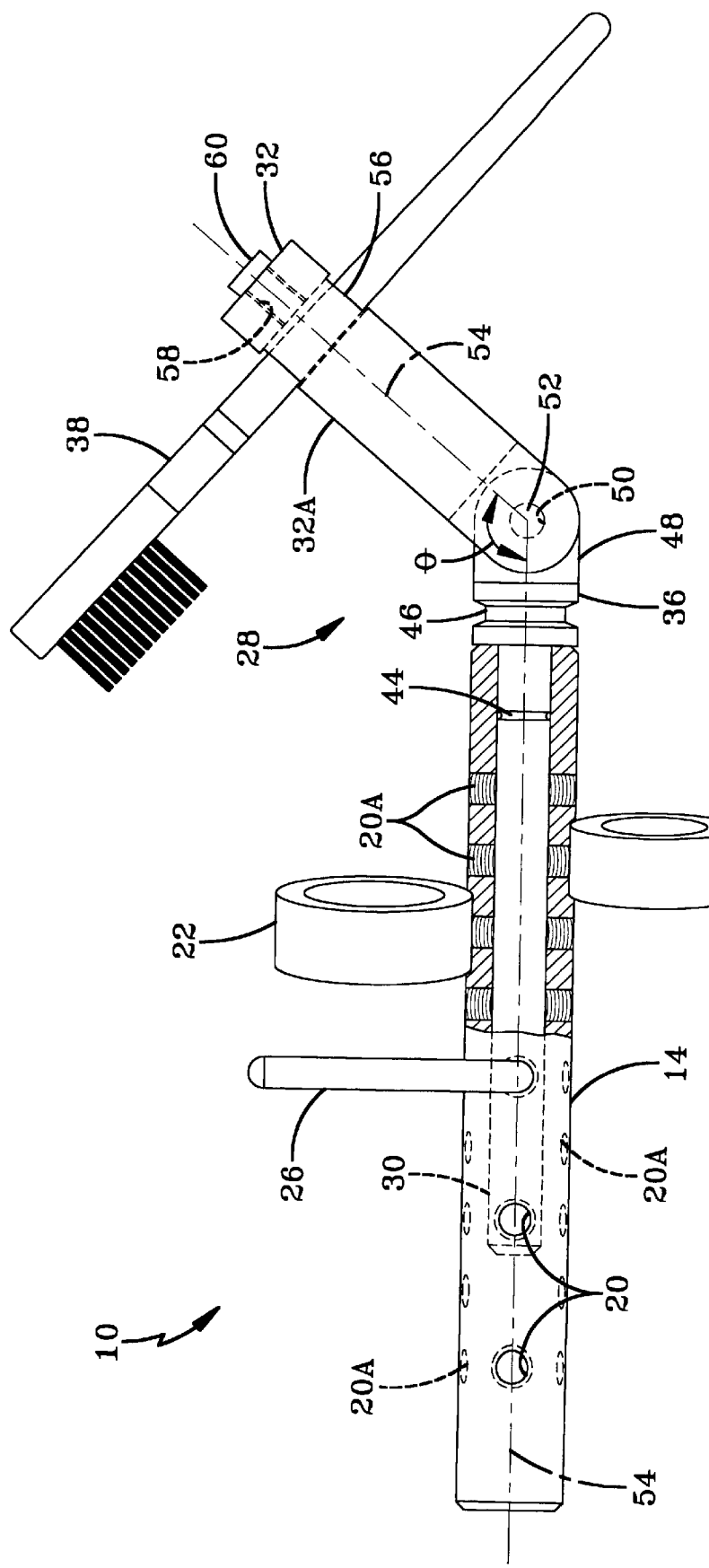
FIG. 4 illustrates the device of the present invention used to hold, capture and control a toothbrush so that it may be more easily manipulated by a physically handicapped person.

FIG. 4 illustrates the extension 32A of holder 28 as being attached to the control area 48 by means of a screw 52 inserted into opening 50. FIG. 4 further illustrates the first and second finger rings 22 and 24 as being threadly engaged in respective apertures 20A, as well as the insert 26 being threadly engaged in one of the apertures 20 and extending into the central bore of the hollow member 14 so as to engage at least part, such as end 30, of the holder 28. FIG. 4 further illustrates that the hollow member 14 and the extension 32A share a common axis 54 with the extension 32A being offset from the holder 14 by an angle θ. FIG. 4 further illustrates that the extension 32A has an opening 56 into which is inserted a toothbrush 38, with the toothbrush 38 being captured by a screw arrangement formed by threads 58 capturing a screw 60 located at the second end 32 of the holder 28.

From FIG. 4 it may be seen that the toothbrush 3 8 may be oriented in any position desired with respect to the finger rings 22 and 24 normally capturing the thumb and forefinger, respectfully, of the physically handicapped person. More particularly, the toothbrush 38 being captured by the extension 32A may be oriented at any angle θ, such as the angle θ shown in FIG. 4 with respect to the member 14, by first moving the extension 32A and then tightening the screw 52. The toothbrush 38 may also be rotated at any relative to the member 14. More particularly, the rotation may be accomplished by removing any frictional engagement between the insert 26 and the holder 28 and then rotating the toothbrush 38 in a clockwise or counterclockwise direction which, in turn, positions the holder 28 at any desired rotational angle. That desired rotational angle is then established for usage by the handicapped person by the tightening of the insert 26 so that it frictionally engages the holder, in particular, first end 30, within the central bore 42 of the hollow member 14. The easy achievable orientation of the instrument, such as toothbrush 38, provided by the device 10 of the present invention allows the toothbrush 38 to be positioned at any orientation that the physically handicapped person feels comfortable with so that the task, such as brushing teeth, is easily facilitated to accommodate the needs of the physically handicapped person. The device 10, in addition to the toothbrush 38, accommodates a multiplicity of instruments that are manipulated by the hand of the physically handicapped person so as to accommodate those daily tasks desired to be performed by the physically handicapped person. The accommodation of a razor 62 may be further described with reference to FIG. 5.

Figure 5:
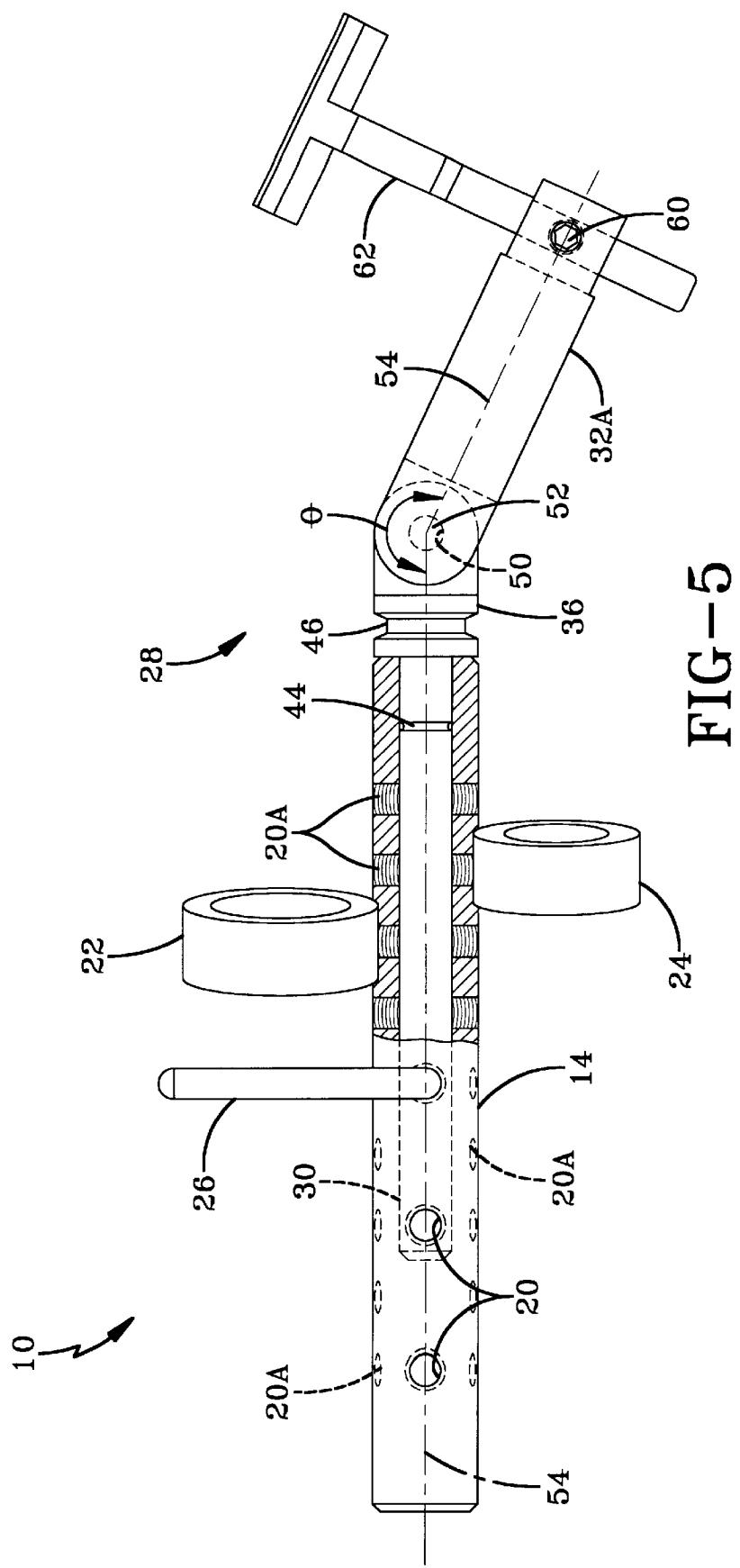
FIG. 5 illustrates the device of the present invention used for capturing, holding, controlling a razor so that it may be more easily manipulated by a physically handicapped person.

FIG. 5 is quite similar to FIG. 4, with the exception that the extension 32A is offset from the member 14 by an angle θ which is greater than 90 degrees. The angle θ being greater than 90 degrees is only shown for illustrated purposes and the desired angle θ is easily selected by the physically handicapped person in the manner as previously described with reference to FIG. 4. Further, the razor 62 may be rotated relative to the hollow member 14 in a manner as described with reference to FIG. 4. A still further instrument, such as a comb 64, is accommodated by the device 10 of the present invention and may be further described with reference to FIG. 6.

Figure 6:
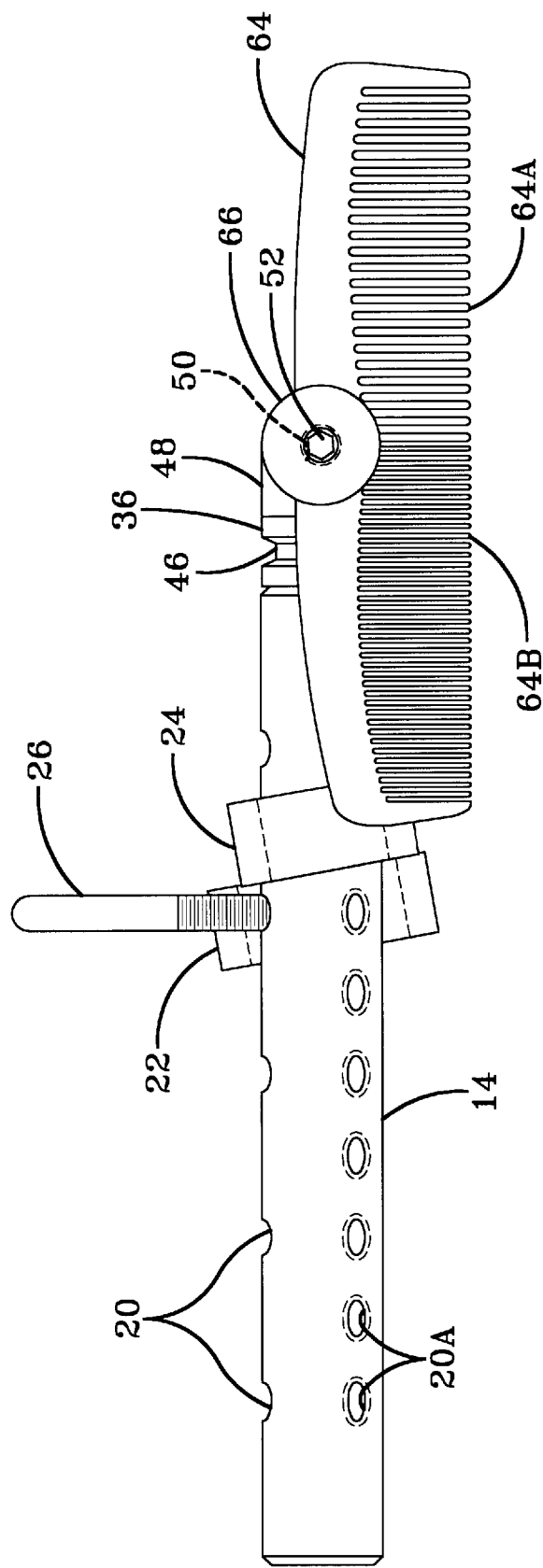
FIG. 6 illustrates the device of the present invention used for capturing, holding, and controlling a comb so that it may be more easily manipulated by a physically handicapped person.

FIG. 6 is quite similar to FIGS. 4 and 5, with the exception that the comb 64 having course and fine teeth 64A and 64B is attached to the holder 18 without the need of the extension 32A. More particularly, the comb 64 is attached to the holder 18 by means of a washer 66 which, in turn, is attached to the control region 48 by means of the screw 52. Again, the comb 64 may be oriented with respect to the hollow member 14 by merely eliminating frictional engagement between the insert 26 and the holder 28, then moving the comb 64 into its desired position, and then re-establishing the frictional engagement between the insert 26 and the holder 28, that is, the end 30 thereof Again, the orientation of the comb 64 in FIG. 6 is for illustrated purposes so as to fit the desired needs of the physically handicapped person, for example, allow the comb to be more closely arranged relative to the finger rings 22 and 24. Further orientations provided by the device 10 of the present invention may be further described with reference to FIGS. 7, 8 and 9.

Figures 7A, 7B, 7C:
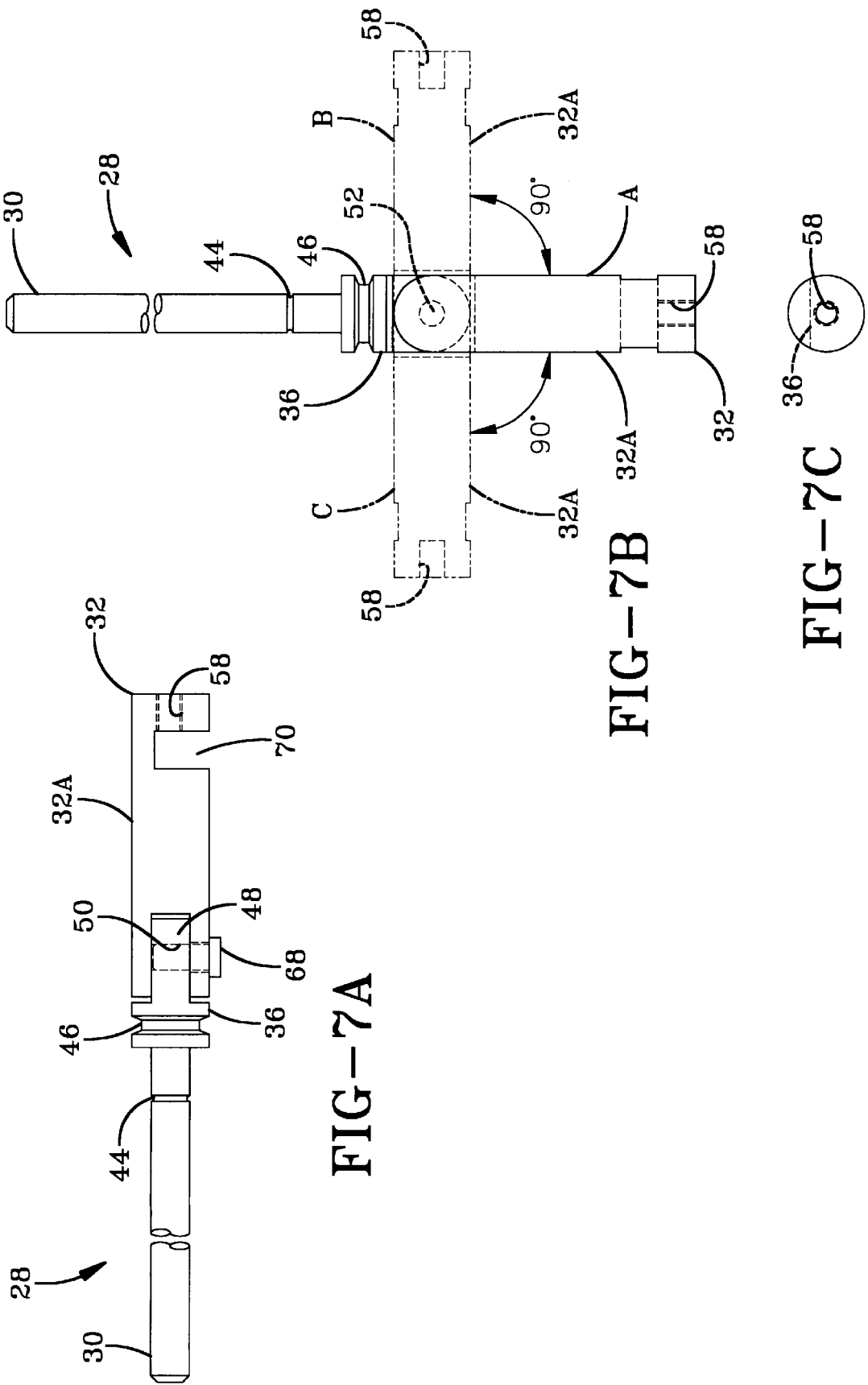
FIG. 7 is composed of FIGS. 7(A), 7(B), and 7(C) which cumulatively illustrate the details of one embodiment of the holder of the present invention.

FIG. 7 is composed of FIGS. 7(A), 7(B), 7(C), which illustrate the rotational capabilities of the extension 32A. More particularly, FIG. 7 illustrates that the extension 32A may be rotated in plus and minus 90 degree segments relative to the first end 30 of the holder 28. This capability is also provided by the embodiments of FIGS. 8 and 9.

As seen in FIG. 7(A), the extension 32A is rotatable and is attached to the control region 40A by means of the screw 52 that is inserted into aperture 50 of the control area 48. It is further seen in FIG. 7(A) that the extension 32A has a cutout 70 located near the second end 32. The rotatability of the extension 32A relative to the first end 30 may be further described with reference to FIG. 7(B).

As seen in FIG. 7(B), the extension 32A has three orientations. The first indicated by reference letter A which is in line with the first end 30, the second orientation being indicated by the letter B and which is displaced 90 degrees, in a clockwise manner, relative to end 30, and in a third orientation being indicated by the letter C and which is oriented 90 degrees counterclockwise relative to the first end 30. The orientations B and C are easily established by first loosening the screw 52 and then rotating the end 32A to achieve its desired position B or C. An end view, that is, the second end 32, of the rotatable extension 32A is shown in FIG. 7(C). The practice of the present invention provides further embodiment that allows for a 90 degree rotation and which may be further described with reference to FIG. 8 which is composed of FIGS. 8(A), 8(B), and 8(C).

FIG. 8 is quite similar to FIG. 7 with the exception that the extension 32A of FIG. 8 includes an opening 72, a groove 74, and a strap 76 which is inserted into the opening 72 and guided by the groove 74. The strap 76 may be used to attach an instrument, such as a mirror to the extension 32A, which, in turn, is attached to the member 14 so as to form one of the embodiments of the device 10 of the present invention. The orientation of the embodiment of FIG. 8 that allows for the plus or minus 90 degrees segments previously discussed with reference to 7(B) is shown in FIG. 8(B). The operation of the device of FIG. 8(B) is similar to that of previously described with reference to FIG. 7(B) and similarly the end view of the embodiment of FIG. 8 shown in FIG. 8(C) is similar to that of FIG. 7(C). A further embodiment of the present invention that provides for the 90 degree segments may be further described with reference to FIG. 9 which is composed of FIGS. 9(A), 9(B), and 9(C).

Figure 9B:
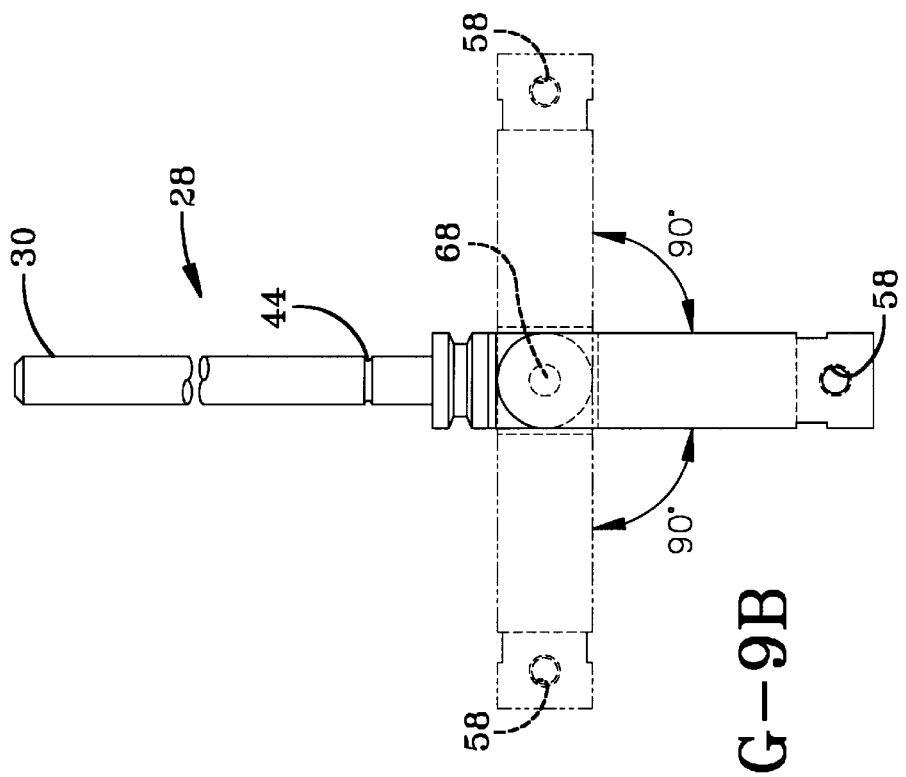
FIG. 9 is composed of FIGS. 9(A), 9(B), and 9(C) that cumulatively illustrates the details of yet another embodiment of the holder of the present invention.
Figure 9C:
Figure 9A:
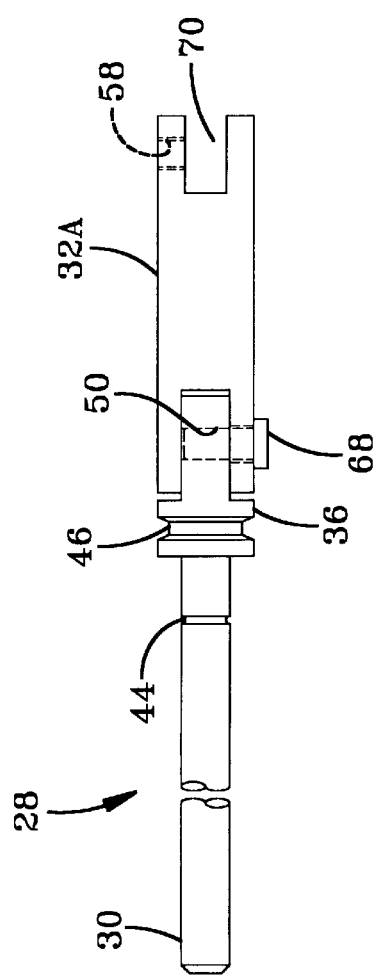

FIG. 9 is quite similar to FIG. 8 with the exception that the embodiment of FIG. 9 has a cutout 78 that extends all the way to the end 32 as shown in FIG. 9(A). The orientation capabilities for the embodiment of FIG. 9 are shown in FIGS. 9(B) and 9(C) that are similar to the description given for FIGS. 7(B) and 7(C) respectively.

In should now be appreciated that the practice of the present invention provides for devices that capture and hold various instruments used by a physically handicapped person and with the device allowing for easier manipulation and control thereof of the instruments.

The present invention also provides for a container 80 for storing the devices of FIGS. 1–9 having the channel 46 adjacent to quick-release mechanism comprising the groove 44 and the spring loaded plungers 40. The container may be described with reference to FIG. 10 composed of FIGS. 10(A) and 10(B).

The container 80 comprises a top 82 that is hingedly attached, by means of hinge 84, to the walls 86 of the container 80. The container 80 has a shelf 88 that includes cutouts 90 into which are placed the devices 10 comprised of member 14 and the channel 46. The container 80 further has clips 92 that allow the container to be conveniently attached to the rest arms of a chair that may be occupied by the physically handicapped person. The container 80 may be further described with reference to FIG. 10(B) which is a view taken along line 10B—10B of FIG. 10(A).

FIG. 10(B) illustrates the extension 32A of holder 28 carrying a razor 62. FIG. 10(B) further illustrates that if an upward movement, indicated by directional arrow 94, is applied to the hollow member 14 of the device 10, the hollow member 14, because of the quick-release mechanism provided by the spring plungers 40 carried in the first end of the member 16 in operative cooperation with the groove 44 of the holder 28, the hollow member 14 is released from the holder 28. The holder 28 remains in a stationary position because the channel 36 is maintained in the cutout 90 on the shelf 88.

It should now be appreciated that the practice of the present invention provides for a container having an interior shelf 88 having cutouts 90 for receiving and capturing the channel 36 of the device 10 so that when any one of the devices 10 is subjected to a rapid vertical movement, such as when indicated by directional arrow 94, the quick-release mechanism of the device 10 is activated and the holder 28 of the device 10 remains in place in the cutout 88 along with the instrument being held, such as the razor 62.

The foregoing description of the specific embodiments of the present invention will so fully reveal the general nature of the invention that others can, by applying current knowledge, be readily modify and/or adapt for various applications such specific embodiments without departing from the general concept, and therefore such adaptations equivalence of the disclosed embodiments. It is therefore understood that the phraseology and terminology employed herein is for the purpose of description and not of limitation.

What I claim is:

1. A device for assisting a physically handicapped person to perform tasks that are managed by the use of the hand having digits of the handicapped person, said device comprising:

(a) a hollow member having first and second ends and a central bore extending at least partially therethrough and encompassing said first end and having predetermined dimensions, said hollow member having a plurality of apertures with threads therein;

(b) first and second rings attached to said member and spaced apart from each other in a predetermined manner and each dimensioned to receive one of the digits of said hand of said handicapped person;

(c) an insert having a threaded end for insertion into and threaded engagement with one of said threaded apertures; and (d) a holder having first and second ends with the first end thereof dimensioned for insertion into said central bore by way of said first end of said hollow member and with the second end thereof having provisions for holding an instrument used in the performance of said tasks managed by the use of said hand of said handicapped person.

2. The device according to claim 1, wherein said first end of said member further comprises at least one spring loaded plunger extending into said central bore thereof and said holder having a groove that is dimensioned to receive and engage said at least one spring loaded plunger.

3. The device according to claim 2, wherein said at least one spring loaded plunger comprises three spring loaded plungers that are spaced apart from each of by about 120 degrees.

4. The device according to claim 1, wherein said first and second rings are rotatably attached to said member.

5. The device according to claim 1, wherein said first ring is dimensioned to receive the thumb of said hand and said second ring is dimensioned to receive the forefinger of said hand.

6. The device according to claim 1, wherein said threaded end of said insert is threaded so as to be capable of extending into said central bore and frictionally engaging a portion of said holder.

7. The device according to claim 1, wherein said second end of said holder further comprises means for being rotated with respect to said first end thereof.

8. The device according to claim 7, wherein said holder has a common axis and said means for rotating allows said second end to be rotated in + and −90 degree segments about said common axis.

* * * * *